United States Patent [19]

DiSabito

[11] Patent Number: 5,197,472
[45] Date of Patent: Mar. 30, 1993

[54] DISPOSABLE LEG PLATE ELECTRODE ASSEMBLY

[75] Inventor: David M. DiSabito, Clarence, N.Y.

[73] Assignee: Graphic Controls Corporation, Buffalo, N.Y.

[21] Appl. No.: 736,473

[22] Filed: Jul. 26, 1991

[51] Int. Cl.$^5$ ............................................. A61B 5/04
[52] U.S. Cl. ................................... 128/644; 128/639; 128/642
[58] Field of Search ................ 128/639, 640, 642, 644

[56] References Cited

U.S. PATENT DOCUMENTS

| | | | |
|---|---|---|---|
| 2,590,876 | 4/1952 | Landauer | 128/417 |
| 2,882,904 | 4/1954 | Rasmussen | 128/418 |
| 3,464,404 | 6/1966 | Mason | 128/2.06 |
| 3,534,727 | 10/1970 | Roman . | |
| 3,717,141 | 2/1973 | Krohn et al. | 128/2.06 |
| 3,812,845 | 5/1974 | Partridge | 128/2.06 |
| 3,888,240 | 6/1975 | Reinhold | 128/2.06 |
| 3,895,635 | 7/1975 | Justus et al. | 128/303.13 |
| 3,973,557 | 8/1976 | Allison | 128/2.06 |
| 3,977,392 | 8/1976 | Manley | 128/2.1 |
| 3,989,035 | 11/1976 | Zuehlsdorff | 128/2.1 |
| 3,993,049 | 11/1976 | Kater | 128/2.06 |
| 4,027,664 | 6/1977 | Heavner et al. | 128/2.06 |
| 4,082,086 | 4/1978 | Page et al. | 128/2.06 |
| 4,121,573 | 10/1978 | Crovella | 128/2.1 |
| 4,121,575 | 10/1978 | Mills et al. | 128/2.06 |
| 4,197,851 | 4/1980 | Fellus | 128/422 |
| 4,209,020 | 6/1980 | Nielsen | 128/640 |
| 5,046,965 | 9/1991 | Neese et al. | 128/642 X |

OTHER PUBLICATIONS

Berkeley Bio-Engineering "Operating the Berkeley 900 Fetal Monitoring System", 1975, Rev. Feb. 23, 1977.

Primary Examiner—Lee S. Cohen
Attorney, Agent, or Firm—Ratner & Prestia

[57] ABSTRACT

A disposable electrode assembly comprising a pair of thin, flexible, foam pads having adhesive on their facing surfaces. Leads from remotely located fetal electrodes are secured between the pads by the adhesive and are in electrical contact with conductive plates also located between the two pads. The lower pad carries a body electrode which is in electrical contact with the patient when the assembly is attached to the patient. Such attachment is assured without using an adhesive on the lower pad which contacts the patient's skin. The conductive plates and the body electrode are electrically connected to a fetal monitoring device by thin conductors also secured between the pads by the adhesive. The thin conductors combine in a cable assembly adapted to connect to the fetal monitoring device.

27 Claims, 3 Drawing Sheets

DISPOSABLE LEG PLATE ELECTRODE ASSEMBLY

BACKGROUND OF THE INVENTION

The present invention relates to an electrode assembly and, more particularly, to a disposable leg plate electrode assembly which is most useful as part of a fetal monitoring system.

Fetal monitoring is a technique which has been used for many years, primarily when a mother is giving birth. The technique is accomplished by attaching one or more electrodes to the fetus. An additional electrode attached to the mother is used to establish a base or reference voltage for the fetal electrodes. The fetal electrodes, via leads passing through the birth canal, and the additional electrode are connected to a fetal monitoring device.

In order to avoid accidentally dislodging the fetal electrodes, past electrode assemblies used a metal base plate strapped to the mother's thigh. The plate carries a pair of insulated connectors which engage the leads passing through the birth canal and connecting to the fetal electrodes. A main cable electrically coupled to the metal base plate and to the connectors is used to link the electrode assembly to the fetal monitoring device. This attachment prevents disengagement of the fetal electrodes in the event that the mother moves relative to the fetal monitoring device.

Although the electrode assembly described above has had some success, it has several drawbacks. The most significant of these drawbacks is its expense: the cost of such devices normally is between $50 and $100. Moreover, although they may be reused, the devices represent a capital investment to a hospital or clinic which cannot be directly charged to the patient. The expense is increased because the plate devices become soiled during use and must be cleaned before being reused. In addition, a hospital or clinic would require numerous identical devices to assure availability during the cleaning process.

An attempt to produce an electrode assembly which can overcome these drawbacks is disclosed in U.S. Pat. No. 4,209,020 issued to Nielson. The Nielson assembly is disposable and less expensive than those devices described above. Nevertheless, it still has practical problems, the two most significant of which are: 1) the way in which the leads from the remote fetal electrodes are attached to the electrode assembly, and 2) the way in which the electrode assembly is attached to the patient.

Nielson uses spring clips to attach the fetal electrode leads to the assembly. These protruding clips complicate both the use of the assembly and its manufacture. As a general rule, of course, the more complicated the manufacturing procedure, the more expensive the item. Nielson also uses an adhesive to attach the assembly to the patient. An adhesive attachment on the patient's skin precludes easy adjustment of the assembly, is uncomfortable for the patient, and risks injury to the patient upon removal.

Thus, the objects of the present invention are to simplify the manufacturing procedure to minimize cost while meeting the patient's needs, especially comfort and the assurance of a continually functional device.

SUMMARY OF THE INVENTION

To achieve these and other objects, and in view of its purposes, the present invention provides a disposable electrode assembly comprising a pair of thin, flexible, foam pads having adhesive on their facing surfaces. Leads from remotely located fetal electrodes are secured between the pads by the adhesive and are in electrical contact with conductive plates also located between the two pads. The lower pad carries a body electrode which is in electrical contact with the patient when the assembly is attached to the patient. Such attachment is assured without using an adhesive on the lower pad which contacts the patient's skin. The conductive plates and the body electrode are electrically connected to a fetal monitoring device by thin conductors also secured between the pads by the adhesive. The thin conductors combine in a cable assembly adapted to connect to the fetal monitoring device.

It is to be understood that both the foregoing general description and the following detailed description are exemplary, but are not restrictive, of the invention.

BRIEF DESCRIPTION OF THE DRAWINGS

The invention is best understood from the following detailed description when read in connection with the accompanying drawing, in which.

DETAILED DESCRIPTION

Figure 1:
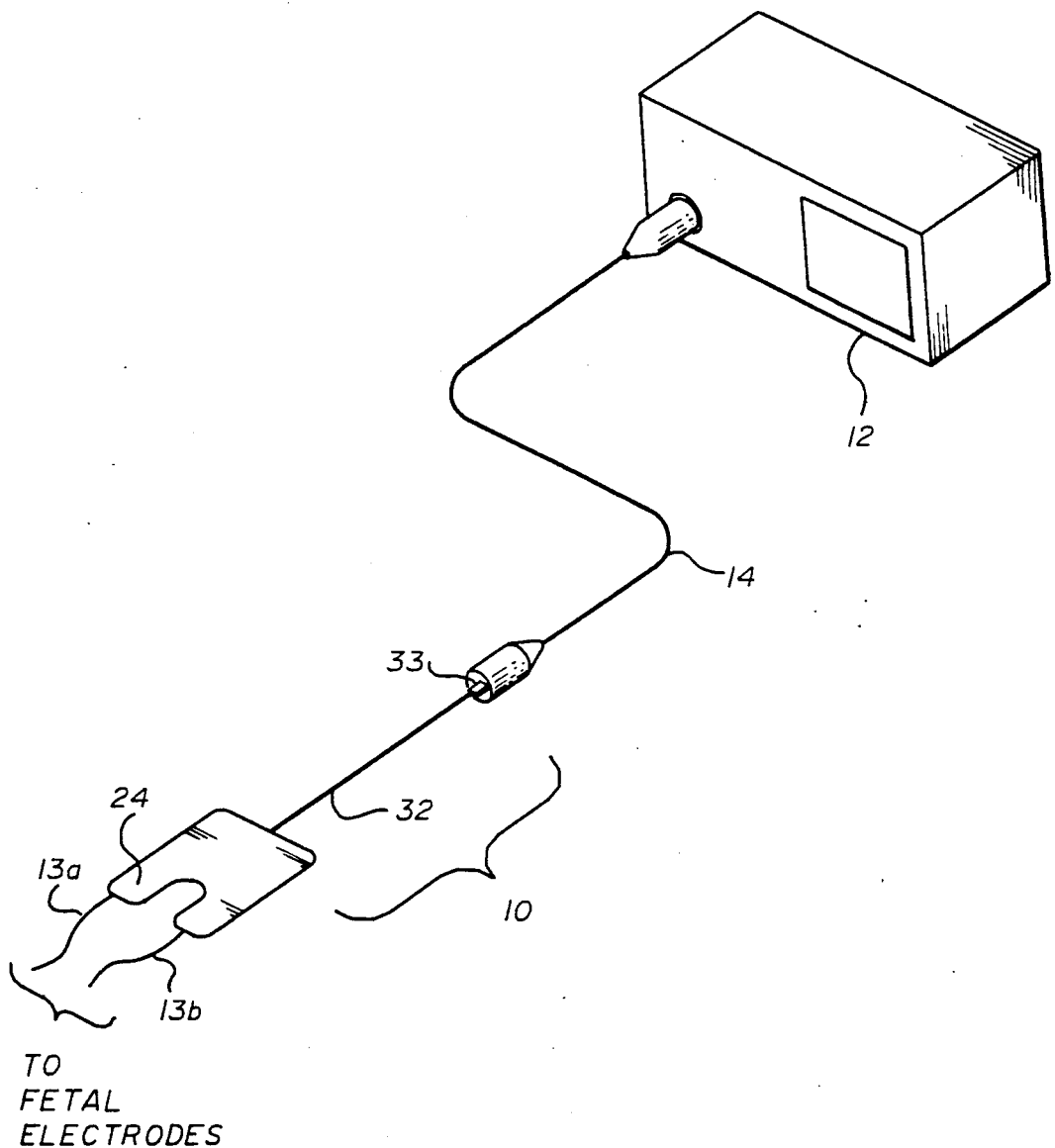
FIG. 1 is a perspective view of an electrode assembly constructed in accordance with the principles of the present invention, illustrating that the assembly is attached to a fetal monitoring device and fetal electrode leads.

Like reference numerals have been used throughout the various figures of the drawing to identify like elements. Shown in FIG. 1 is an electrode assembly 10 constructed in accordance with the present invention. Electrode assembly 10 is connected to fetal monitoring device 12 via cable 14. Also shown connected to electrode assembly 10 are leads (wires) 13a, 13b coming from remotely located fetal electrodes (not shown).

Figure 2:
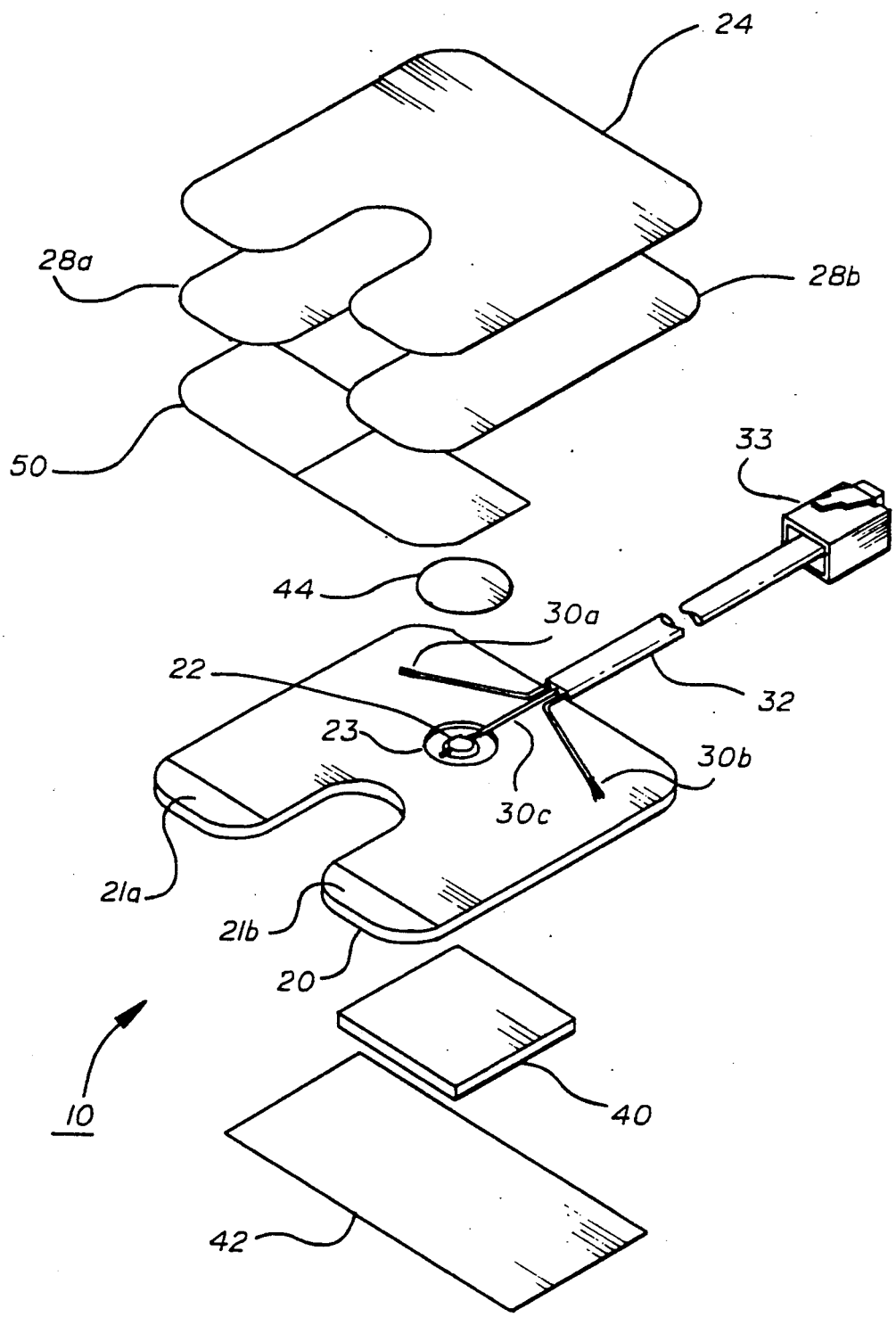
FIG. 2 is a perspective view of a disassembled electrode assembly of the present invention.

As shown in FIG. 2, electrode assembly 10 includes a pair of foam pads 20, 24. The lower pad 20 has an adhesive on its upper surface and no adhesive on its lower surface. Upper pad 24 has an adhesive on its lower surface and, in the preferred embodiment, is covered with vinyl on its upper surface.

By way of example and not limitation, pads 20, 24 may be of any suitable shape. In the preferred embodiment, however, pads 20, 24 are identically shaped rectangles with a pair of tabs 21a, 21b extending from one side. One possible set of dimensions for the pads are 45 mm by 75 mm. Tabs may be provided, for example, by forming a central opening in the pad about 15 mm deep and 25 mm wide. Each pad 20, 24 is about 1 mm thick.

Pad 20 has a centrally located aperture 23 from its upper surface through to its lower surface for carrying a body electrode 22. Body electrode 22 protrudes through the lower surface of pad 20 for contacting a patient. In the preferred embodiment, body electrode 22 has a silver/silver chloride coating; as known to those persons skilled in the art, most any suitable conductive material would suffice.

To enhance electrical contact between body electrode 22 and the patient, a conductive gel 40 covers the portion of body electrode 22 protruding from the lower surface of pad 20. Conductive gel 40, in the preferred embodiment a hydrogel, is protected by a removeable cover 42 until the electrode assembly is put into use.

Body electrode 22 is insulated from above by an insulating lid 44 which covers the aperture in pad 20 on its upper surface. In the preferred embodiment, insulating lid 44 is vinyl; however, as known by those skilled in the art, most any suitable insulating material would suffice.

Two conductive plates 28a, 28b are sandwiched between pads 20, 24 and are fixed by the adhesive on the upper and lower surfaces, respectively, of those pads. Portions of conductive plates 28a, 28b are separated from the adhesive on the upper surface of pad 20 by a removable cover or release liner 50. Release liner 50 can be a single piece of plastic or, in an alternate embodiment, a plurality of pieces—one for each conductive plate 28a, 28b. Leads 13a, 13b from the remote fetal electrodes (not shown) are inserted between the separated portions of conductive plates 28a, 28b and release liner 50. When release liner 50 is removed and contact is formed between conductive plates 28a, 28b and the adhesive on the upper surface of lower pad 20, leads 13a, 13b simultaneously are secured between conductive plates 28a, 28b and pad 20 and are placed in electrical contact with conductive plates 28a, 28b.

Connected to conductive plates 28a, 28b and to body electrode 22, respectively, are three, thin conductors 30a, 30b, 30c. These conductors, preferably separately insulated wires, are joined in a cable assembly 32. Cable assembly 32 terminates in a multi-terminal or jack 33 for the purpose of being electrically connected to a fetal monitoring device 12.

Figure 3:
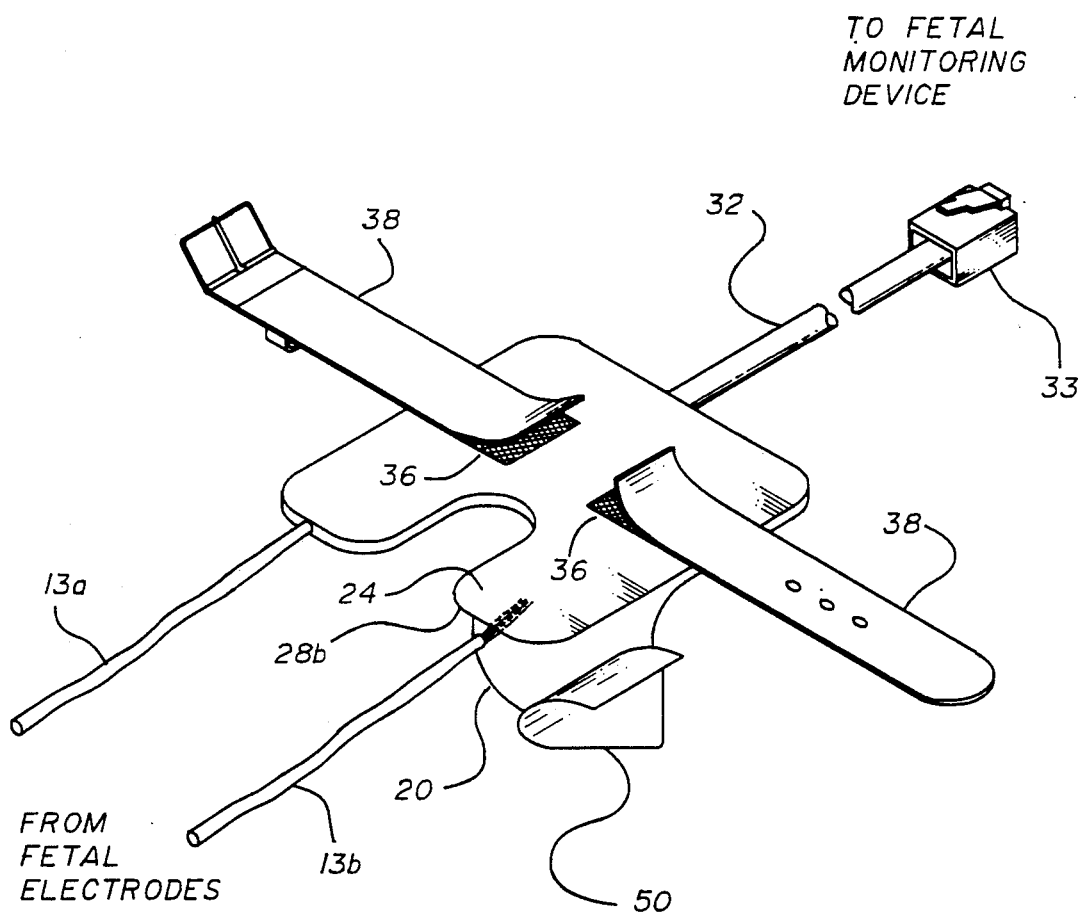
FIG. 3 is a perspective view of the electrode assembly with the fetal electrode leads inserted, also showing one embodiment of the structure disclosed for securing the electrode assembly to a patient.

Attached to the upper surface of pad 24 are the structural elements necessary to secure electrode assembly 10 to the patient. In the preferred embodiment, as shown in FIG. 3, one or more Velcro ® strips 36 are affixed to the upper surface of pad 24. An adjustable belt 38, one side of which is formed of a material which sticks to Velcro ® strips 36, is used for securing electrode assembly 10 to a patient without using a skin-contacting adhesive. Other structural elements possible to perform the securing function would be known by those persons skilled in the art. Belt loops, for example, could be formed on the upper surface of pad 24 into which a strap could be inserted. Tape might also be used.

The electrode assembly 10 described above is used in the following manner. First, the removable cover 42 protecting conductive gel 40 is removed, thus exposing the conductive gel. Then electrode assembly 10 is attached to the patient's thigh by way of the Velcro ® strips 36 and adjustable belt 38. Once electrode assembly 10 is securely held in place by adjustable belt 38, conductive gel 40 contacts the patient and functions to enhance electrical contact between the patient and body electrode 22.

After the fetal electrodes have been applied to the fetus, leads 13a, 13b extending from the fetus are inserted between release liner 50 and conductive plates 28a, 28b. Release liner 50 is then removed from the upper surface of pad 20, exposing the adhesive under release liner 50. Pad 20 and conductive plates 28a, 28b are pressed together to sandwich leads 13a, 13b, thus securing the leads and electrically connecting them to conductive plates 28a, 28b.

The remaining step is to connect electrode assembly 10 to fetal monitoring device 12. That connection is made through cable assembly 32 by plugging jack 33 at the end of cable assembly 32 into a complementary plug in fetal monitoring device 12, or into an extension cable 14 connected to that device.

It should be readily apparent that electrode assembly 10 can be made relatively inexpensively. Consequently, electrode assembly 10 can be used once and discarded; it is disposable.

Although the present invention has been described with specific reference for use with a fetal monitoring device, it should be readily apparent that the invention may have numerous other uses. For example, the electrode assembly could be used with the appropriate equipment to produce an electrocardiogram. If so used, body electrode 22 on lower pad 20 of electrode assembly 10 itself will function as one of the body electrodes. The wires leading to other electrodes placed on other parts of the patient's body would be connected to electrode assembly 10 at conductive plates 28a, 28b.

Although the invention is illustrated and described herein as embodied in a disposable electrode assembly having a pair of pads, a body electrode carried by the lower pad, separate conductive plates carried by the upper pad to which leads from remotely located electrodes are attached when sandwiched between the pads and held in position by adhesive, wires connecting the body electrode and plates to a cable assembly and, in turn, to an external monitor, and structure attached to the upper surface of the top pad for securing the assembly to the patient without using an adhesive, the invention is nevertheless not intended to be limited to the details shown. Rather, various modifications may be made in the details within the scope and range of equivalents of the claims and without departing from the spirit of the invention.

What is claimed:

1. A disposable electrode assembly for contacting a patient and for receiving electrical signals from at least one remotely located electrode through a lead connected to each remotely located electrode, said assembly comprising:
   a) a first thin, flexible, non-conductive pad having a lower surface for contacting said patient without adhesive and an upper surface having an adhesive;
   b) a body electrode carried by said first pad and adapted to be in electrical contact with said patient through a skin-contacting surface when said assembly is secured to said patient;
   c) a second thin, flexible, non-conductive pad having a lower surface with an adhesive facing said upper surface of said first pad and an upper surface;
   d) a separate, electrically isolated conductive plate for each lead, said plate attached to said lower surface of said second pad having adhesive and adapted to electrically engage said lead when said lead is inserted between said plate and said upper surface of said first pad and is thereafter adhesively secured between said upper surface of said first pad having adhesive and said plate;
   e) separate, insulated wires electrically engaging each said plate and said body electrode;
   f) a cable assembly joining said separate wires and providing electrical connections to an external monitoring device; and g) means for securing said assembly to said patient, said securing means being carried by said upper surface of said second pad.

2. A disposable electrode assembly as claimed in claim 1 further comprising a thin layer of non-adhesive, conductive gel covering said skin-contacting surface of said body electrode for enhancing electrical contact between said body electrode and said patient.

3. A disposable electrode assembly as claimed in claim 2 wherein said gel is hydrogel.

4. A disposable electrode assembly as claimed in claim 2 further comprising a removable cover protecting said thin layer of gel before use.

5. A disposable electrode assembly as claimed in claim 1 wherein said body electrode has a silver/silver chloride coating.

6. A disposable electrode assembly as claimed in claim 1 wherein said first pad has an aperture for carrying said body electrode.

7. A disposable electrode assembly as claimed in claim 6 further comprising an insulating lid covering the surface of said body electrode opposite its skin-contacting surface.

8. A disposable electrode assembly as claimed in claim 1 further comprising a removable cover separating a portion of each said conductive plate from said upper surface of said first pad having adhesive before said lead is inserted between said plate and said upper surface of said first pad.

9. A disposable electrode assembly as claimed in claim 1 wherein said first and said second pads have identical shapes.

10. A disposable electrode assembly as claimed in claim 1 wherein said first and said second pads each have corresponding tabs and each said plate is attached to an individual tab formed in said lower surface of said second pad having adhesive.

11. A disposable electrode assembly as claimed in claim 1 wherein said insulated wires lie, and are adhesively held in position, between said first and said second pads.

12. A disposable electrode assembly as claimed in claim 1 wherein said securing means includes at least one Velcro ® strip carried by said upper surface of said second pad and an adjustable strap engaging said strip.

13. A disposable electrode assembly as claimed in claim 1 wherein said plate is silver.

14. A disposable electrode assembly as claimed in claim 1 wherein said first pad is foam.

15. A disposable electrode assembly as claimed in claim 1 wherein said second pad is vinyl-covered foam.

16. A disposable electrode assembly for contacting a patient and for receiving electrical signals from at least one remotely located electrode through a lead connected to each remotely located electrode, said assembly comprising:
 a) a first thin, flexible, non-conductive pad having a lower surface for contacting said patient without adhesive and an upper surface having an adhesive;
 b) a body electrode carried by said first pad and adapted to be in electrical contact with said patient through a skin-contacting surface when said assembly is secured to said patient;
 c) a thin layer of non-adhesive, conductive gel covering said skin-contacting surface of said body electrode for enhancing electrical contact between said body electrode and said patient;
 d) a removable cover protecting said thin layer of gel before use;
 e) a second thin, flexible, non-conductive pad having a lower surface with an adhesive facing said upper surface of said first pad and an upper surface;
 f) a separate, electrically isolated conductive plate for each lead, said plate attached to said lower surface of said second pad having adhesive and adapted to electrically engage said lead when said lead is inserted between said plate and said upper surface of said first pad and is thereafter adhesively secured between said upper surface of said first pad having adhesive and said plate;
 g) a removable cover separating a portion of each said conductive plate from said upper surface of said first pad having adhesive before said lead is inserted between said plate and said upper surface of said first pad;
 h) separate, insulated wires electrically engaging each said plate and said body electrode;
 i) a cable assembly joining said separate wires and providing electrical connections to an external monitoring device; and
 j) means for securing said assembly to said patient, said securing means being carried by said upper surface of said second pad.

17. A disposable electrode assembly as claimed in claim 16 wherein said gel is hydrogel.

18. A disposable electrode assembly as claimed in claim 16 wherein said body electrode has a silver/silver chloride coating.

19. A disposable electrode assembly as claimed in claim 16 wherein said first and said second pads have identical shapes.

20. A disposable electrode assembly as claimed in claim 16 wherein said first and said second pads each have corresponding tabs and each said plate is attached to an individual tab formed in said lower surface of said second pad having adhesive.

21. A disposable electrode assembly as claimed in claim 16 wherein said insulated wires lie, and are adhesively held in position, between said first and said second pads.

22. A disposable electrode assembly as claimed in claim 16 wherein said first pad has an aperture for carrying said body electrode.

23. A disposable electrode assembly as claimed in claim 22 further comprising an insulating lid covering the surface of said body electrode opposite its skin-contacting surface.

24. A disposable electrode assembly as claimed in claim 16 wherein said securing means includes at least one Velcro ® strip carried by said upper surface of said second pad and an adjustable strap engaging said strip.

25. A disposable electrode assembly as claimed in claim 16 wherein said plate is silver.

26. A disposable electrode assembly as claimed in claim 16 wherein said first pad is foam.

27. A disposable electrode assembly as claimed in claim 16 wherein said second pad is vinyl-covered foam.

* * * * *